United States Patent [19]

Steer et al.

[11] Patent Number: 4,834,732
[45] Date of Patent: May 30, 1989

[54] OSTOMY COUPLING

[75] Inventors: Peter L. Steer; Neil P. Wiltshire, both of Surrey, England

[73] Assignee: E. R. Squibb and Sons, Inc., Princeton, N.J.

[21] Appl. No.: 71,435

[22] Filed: Jul. 9, 1987

[30] Foreign Application Priority Data

Jul. 31, 1986 [GB] United Kingdom ................. 8618693
Aug. 13, 1986 [GB] United Kingdom ................. 8619716

[51] Int. Cl.⁴ ............................................. A61F 5/448
[52] U.S. Cl. .................................... 604/342; 604/338; 604/905
[58] Field of Search ............................... 604/338–345, 604/905

[56] References Cited

U.S. PATENT DOCUMENTS 3,736,934 6/1973 Hennessy ............................. 604/342
4,460,363 7/1984 Steer et al. .

FOREIGN PATENT DOCUMENTS 0135269 6/1984 European Pat. Off. .
3417183 11/1985 Fed. Rep. of Germany ...... 604/342
802823 9/1936 France ................................. 604/338
3427 8/1985 PCT Int'l Appl. ................. 604/342
1021145 3/1966 United Kingdom .
1099455 1/1968 United Kingdom .
1568860 6/1980 United Kingdom .
1579875 11/1980 United Kingdom .
2121902 7/1985 United Kingdom .
2177926 2/1987 United Kingdom .

Primary Examiner—Albert W. Davis, Jr.
Attorney, Agent, or Firm—Lawrence S. Levinson; Robert E. Lee, Jr.

[57] ABSTRACT

A three part ostomy coupling has a first part having a flange, a central chute and an array of space projections. A second part has a peripheral seal for engaging and surrounding the outer wall of the chute an outwardly projecting rim which can be snap fitted on the space projection. A third part is rotatable to effect a positive lock between the rim the projections, for example by deforming the projections inwardly.

6 Claims, 2 Drawing Sheets

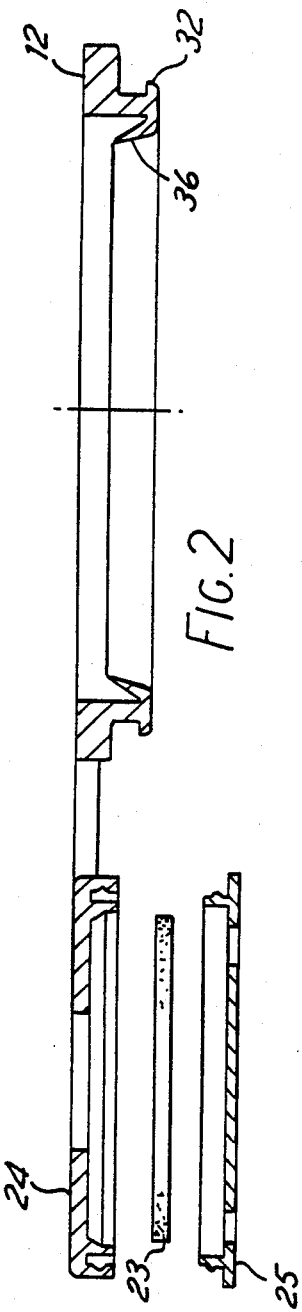
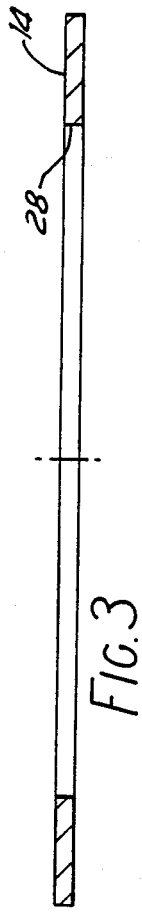
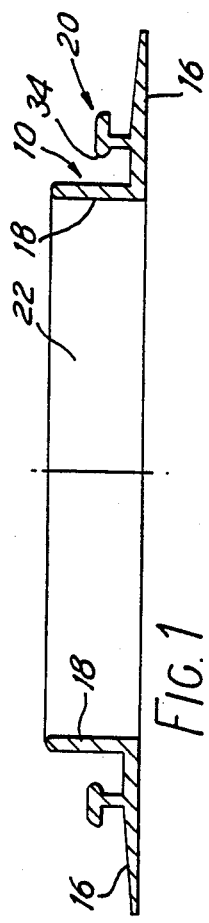
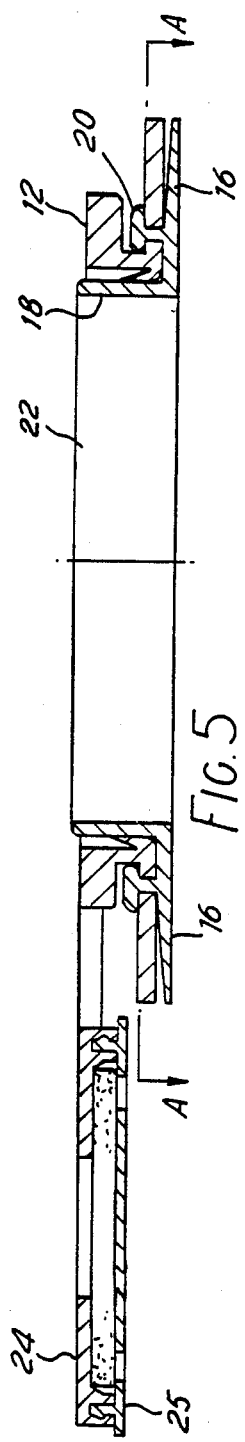

1

OSTOMY COUPLING

BACKGROUND OF THE INVENTION

The present invention relates to a coupling for releasibly connecting a bag or pouch for receiving discharged waste to a pad. The pad is attached to the body of a wearer. Such bags are often called ostomy bags.

As is explained in U.K. Pat. No. 2,121,902 desirable features of an ostomy coupling are that it is easily coupled and uncoupled for changing or emptying of the bag, has good security of attachment and sealing, and has a flat design so that the bag is unobtrusive when worn under light garments or sports clothing. It has been proposed that an ostomate should wear a pad of medical/surgical adhesive material surrounding his stoma and that an ostomy bag or pouch should be connected thereto. In British Pat. Nos. 1,021,145 and 1,099,455 there are proposals for achieving this. A simple coupling using relative rotation of its two parts for connection and disconnection is disclosed in British Pat. No. 1,579,875.

SUMMARY OF THE INVENTION

According to the present invention, there is provided a three-part ostomy coupling which has a first part having a flange, a central chute, and an array of spaced projections; a second part having a peripheral seal for engaging and surrounding the outer wall of the chute and an outwardly-projecting rim capable of a snap-fit with the spaced projections; and a third part which is rotatable to effect a positive lock between the rim and the projections.

In another aspect, the invention provides a three-part ostomy coupling in which rotation of a cam ring to one position prevents the disengagement of the two parts of the coupling and to another position allows the parts to be sprung apart manually.

BRIEF DESCRIPTION OF THE DRAWINGS

In the Drawings:

FIG. 1 shows in cross-sectional view one example of a first part which is preferably but not necessarily a body side coupling element;

FIG. 2 is a similar view of a second part usable in an example of the invention;

FIG. 3 is a similar view of a third part, the common axis of the stomal aperture being shown in these figures as a vertical chain-dotted line; and FIGS. 4 and 5 are respectively diagrammatic views mutually at right angles of an assembled coupling according to the invention, FIG. 4 being a cross-section on the line A—A seen in FIG. 5.

DETAILED DESCRIPTION OF THE PREFERRED EMBODIMENT

Figure 4:
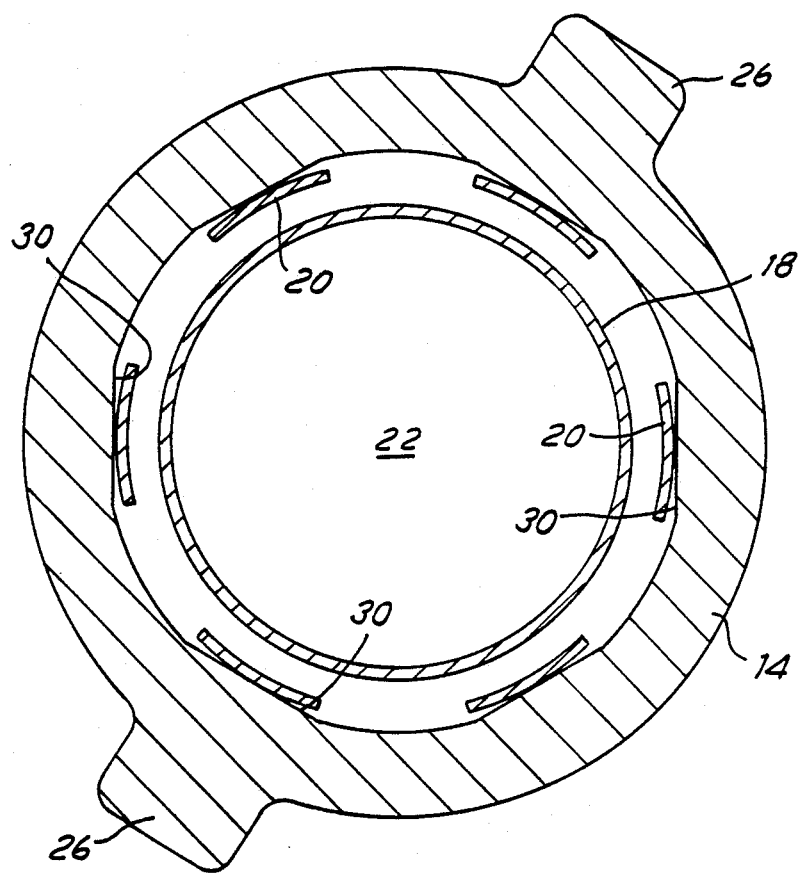

The illustrated ostomy coupling includes a first coupling element 10, a second coupling element 12, and a locking ring 14, also called a "cam ring" herein. The first coupling element 10 is the body side member and has a flange 16, a central chute 18, and a series of spaced projections 20 surrounding the chute 18. Preferably, the first coupling element 10 is made in one piece as a molding of plastic. The projections 20 are arranged to surround the chute 18 and are arcuate in form (see FIG. 4). The projections 20 are spaced from one another in a peripheral direction by a distance greater than, preferably slightly greater than, the arcuate extent of each projection 20. Preferably, the projections 20 are all of equal arcuate length, but this is not essential. The chute 18 is shown as cylindrical surrounding the stomal orifice 22, but minor departures from circularity are considered to be within the scope of the present invention.

The second element 12 of the coupling illustrated in FIG. 2 is the bag side coupling element 12. In this embodiment of the invention it is similar to the one described and illustrated in British Pat. No. 2,121,902, FIG. 5, to which the reader is referred for a detailed description. The bag side coupling element 12 includes a filter housing 24. This may take the form shown in U.K. patent application No. 8531257. The housing 24 is intended to contain filter media 23 and has a lid or cover 25. The presence of a filter housing 24 is not essential to the present invention. The advantages of locking the two coupling elements 10, 12 together in the manner described are also obtained in ostomy couplings which do not have a filter housing. The second coupling element 12 includes a flexible seal strip 36. This part 36 on the second coupling element 12 is a flexible and deflectable sealing means, and may be of the kind disclosed and illustrated in British Pat. No. 1568860.

The coupling ring 14 is a plain flat ring having ears 26, as shown in FIG. 4, and having a central hole therein bounded by a wall 28 which is part circular with the part circular portions being joined by straight portions 30, as shown in FIG. 4. These straight portions 30, in effect, act as cams and in one rotary position of the ring 14, namely the position shown in FIG. 4 prevent the projections 20 from being forced radially outwardly and in another rotary position, that is to say in a position where the flat portions 30 are located in the spaces between the projections 20, the restraint against outward movement of the projections 20 is removed.

It will be understood from this that the function of the ring 14 is to provide a positive locking, and the lock position (to which it is moved by the wearer of the bag gripping the ears 26 and twisting about the axis of the stomal orifice) is that shown in FIG. 4. In the unlocked position of the ring 14, the first and second parts 10, 12 of the coupling can be separated from each other manually by an axial pull which results in a slight deformation of the projections 20 permitting the rim 32 to spring past the inwardly extending parts 34 of the respective projection.

It has been previously suggested, for example in British patent specifications Nos. 1021145 and 1579875, to employ a relative rotation to effect a locking between two parts of an ostomy coupling. It is believed that neither of these prior proposals was effective in practice because of difficulty in operation and unreliability of sealing against egress of liquid. On the other hand, the invention disclosed herein embodies well tried techniques which have proven successful, coupling with the valuable extra feature of a cam ring or locking ring which provides a positive assurance that the parts of the coupling cannot be separated except when desired by the wearer.

We claim:

1. A three-part ostomy coupling which has a first part having a flange, a central chute, and an array of spaced projections; a second part having a peripheral seal for engaging and surrounding the outer wall of the chute and an outwardly-projecting rim capable of a snap-fit with the spaced projections; and a third part which is rotatable to effect a positive lock between the rim and the projections.

2. A coupling according to claim 1 in which the said third part is formed by a cam ring.

3. A coupling according to claim 1 or any claim dependent thereon in which the third part is operative to deform the spaced projections so that they overlap the said rim.

4. An ostomy coupling comprising two coupling parts and a cam ring in which rotation of said cam ring to one position prevents the disengagement of said two parts of the coupling and to another position allows the parts to be sprung apart manually.

5. A coupling according to claim 2 in which the said two parts are of resilient plastics material and consist of a first part forming a wall around a stomal orifice and having an outwardly projecting rim extending from the wall way from the stomal orifice and a second part formed by a plurality of arcuate walls each having an inwardly projecting portion which can be sprung past the rim to separate the two parts due to the resilience of the material.

6. A coupling according to claim 2 or 4 in which the cam ring has a cam surface formed by cylindrical surfaces alternating with flat surfaces.

* * * * *